(12) United States Patent
Chegini et al.

(10) Patent No.: US 7,049,069 B2
(45) Date of Patent: May 23, 2006

(54) DETECTING AND TREATING REPRODUCTIVE TRACT DISORDERS

(75) Inventors: Nasser Chegini, Gainesville, FL (US); Robert Stanford Williams, Gainesville, FL (US); Barry Ripps, Pensacola, FL (US)

(73) Assignee: University of Florida, Gainesville, FL (US)

( * ) Notice: Subject to any disclaimer, the term of this patent is extended or adjusted under 35 U.S.C. 154(b) by 491 days.

(21) Appl. No.: 10/198,306

(22) Filed: Jul. 17, 2002

(65) Prior Publication Data

US 2003/0032044 A1 Feb. 13, 2003

Related U.S. Application Data

(60) Provisional application No. 60/306,133, filed on Jul. 17, 2001.

(51) Int. Cl.
*C12Q 1/68* (2006.01)
*G01N 33/53* (2006.01)

(52) U.S. Cl. .......................................... 435/6; 435/7.95
(58) Field of Classification Search .................... 435/6, 435/7.95
See application file for complete search history.

(56) References Cited

U.S. PATENT DOCUMENTS

| | | |
|---|---|---|
| 3,997,391 A | 12/1976 | Ortolani |
| 5,596,072 A | 1/1997 | Culpepper et al. |
| 5,623,555 A | 4/1997 | Nelson et al. |
| 5,830,453 A | 11/1998 | Badr et al. |
| 5,874,566 A | 2/1999 | Veerapanane et al. |
| 5,985,663 A | 11/1999 | Bennett et al. |
| 5,986,059 A | 11/1999 | Shanafelt et al. |
| 6,001,973 A | 12/1999 | Strom et al. |
| 6,013,480 A | 1/2000 | Grabstein et al. |
| 6,027,720 A | 2/2000 | Kuga et al. |
| 6,028,176 A | 2/2000 | Greve et al. |
| 6,143,871 A | 11/2000 | Bonnefoy et al. |
| 6,165,466 A | 12/2000 | Grabstein et al. |
| 6,168,783 B1 | 1/2001 | Grabstein et al. |
| 6,177,079 B1 | 1/2001 | Grabstein et al. |
| 6,184,359 B1 | 2/2001 | Grabstein et al. |
| 6,190,901 B1 | 2/2001 | Sundick et al. |

FOREIGN PATENT DOCUMENTS

WO WO 99/51643 10/1999

OTHER PUBLICATIONS

Vignali and G. Centinaio, "Studio dell'efficacia della somministrazione di progesterone naturale per via vaginale nella paziente affetta da poliabortivita da causa ormonale, " Minerva Ginecologica, 52: 367-374, 2000.
Sagol et al., "The Effect of Medroxyprogesterone Acetate and Heparin in the Prevention of Postsurgical Adhesion Formation in the Rat Uterine Model," J. Obstet. Gynaecol. Res., 25: 287-293, 1999.
Grabstein et al., "Cloning of a T Cell Growth Factor That Interacts with the µ Chain of the Interleukin-2 Receptor," Science, 264: 965-968, 1994.
Clark and K. Croitoru., "TH1/TH2,3 Imbalance due to Cytokine-Producing NK, γδ T and NK-γδ T cells in Murine Pregnancy Decidua in Success of Failure of Pregnancy," American Journal of Reproduction Immunology, 45: 257-265, 2001.
Makhseed et al., "Mitogen-Induced Cytokine Responses of Maternal Peripheral Blood Lymphocytes Indicate a Differential Th-Type Bias in Normal Pregnancy and Pregnancy Failure," American Journal of Reproductive Immunology, 42: 273-281, 1999.
Verma et al., "Human Decidual Natural Killer Cells Express the Receptor for and Respond to the Cytokine Interleukin 15," Biology of Reproduction, 62: 959-968, 2000.
Odukoya et al., "The Pattern of cytokine mRNA expression in ovarian endometriomata," Molecular Human Reproduction, 3: 393-397, 1997.
Bedaiwy et al., "Prediction of endometriosis with serum and peritoneal fluid markers: a prospective controlled trial," Human Reproduction, 17: 426-431, 2002.

(Continued)

*Primary Examiner*—Janet L. Andres
*Assistant Examiner*—Gyan Chandra
(74) *Attorney, Agent, or Firm*—Saliwanchik, Lloyd & Saliwanchik

(57) ABSTRACT

Methods for detecting and treating a female reproductive tract disorder relate to the discovery that IL-13 and IL-15 are differentially expressed in biological samples from subjects suffering from a reproductive tract disorder compared to samples from healthy subjects. A female reproductive tract disorder is detected by providing a biological sample derived from the subject; analyzing the expression of IL-13 and/or IL-15 in the sample; and correlating the expression of the cytokine with the presence or absence of the female reproductive tract disorder in the subject. Cytokine expression is modulated in female reproductive tract tissue by contacting the tissue with an agent that modulates expression of IL-13 and/or IL-15 in the tissue.

12 Claims, 11 Drawing Sheets

OTHER PUBLICATIONS

Makhseed et al., "Circulating cytokines and CD 30 in normal human pregnancy and recurrent spontaneous abortions," Human Reproduction, 15: 2011-2017, 2000.

Bulfone-Paus et al., "Death deflected: IL-15 inhibits TNF-α-mediated apoptosis in fibroblasts by TRAF2 recruitment to the IL-15Rα chain," The FASEB Journal, 13: 1575-1585, 1999.

Fehniger, T. and Caligiuri, M., "Interleukin 15: biology and relevance to human disease," Blood, 97: 14-32, 2001.

Jensen, P., "The Interleukin 13 Receptor Complex," Stem Cells, 18: 61-62, 2000.

Mijatovic et al., "Interleukin-4 and -13 Inhibit Tumor Necrosis Factor-α mRNA Translational Activation in Lipopolysaccharide-induced Mouse Macrophages," The Journal of Biological Chemistry, 272: 14394-14398, 1997.

Muchamuel et al., "IL-13 Protects Mice from Lipopolysaccharide-Induced Lethal Endotoxemia," The Journal of Immunology, 158: 2898-2903, 1997.

Di Santo et al., "IL-13 Inhibits TNF Production but Potentiates That of IL-6 In Vivo and Ex Vivo in Mice," The Journal of Immunology, 159: 379-382, 1997.

de Waal Malefyt et al., "Effects of IL-13 on Phenotype, Cytokine Production, and Cytotoxic Function of Human Monocytes," The Journal of Immunology, 151:6370-6381, 1993.

Waldmann, T.A. and Tagaya, Y., "The Multifaced Regulation of Interleukin-15 Expression and the Role of This Cytokine in NK Cell Differentiation and Host Response to Intracellular Pathogens," Annu. Rev. Immunol. 17: 19-49, 1999.

Vainer et al., "Colonic Expression and Synthesis of Interleukin 13 and Interleukin 15 in Inflammatory Bowel Disease," Cytokine, 12: 1531-1536, 2000.

Okada et al., "Expression of interleukin-15 in human endometrium and decidua," Molecular Human Reproduction, 6: 75-80, 2000.

Kitaya et al., "IL-15 Expression at Human Endometrium and Decidua," Biology of Reproduction, 63: 683-687, 2000.

Okada, et al., "Progesterone Enhances Interleukin-15 Production in Human Endometrial Stromal Cells in Vitro," The Journal of Clinical Endocrinology & Metabolism, 85: 4765-4770, 2000.

McLaren et al., "Decreased levels of the potent regulator of monocyte/macrophage activation, interleukin-13, in the peritoneal fluid of patients with endometriosis," Human Reproduction, 12: 1307-1310, 1997.

Arici et al., "Increased levels of interleukin-15 in the peritoneal fluid of women with endometriosis: inverse correalation with stage and depth of invasion," Human Reproduction, 18: 429-432, 2003.

Chegini et al., "Differential Expression of Interleukins (IL)—13 and IL-15 in Ectopic and Eutopic Endometrium of Women With Endometriosis and Normal Fertile Women," AJRI, 49: 75-83, 2003.

Guerra-infante et al., "Tumor Necrosis Factor in Peritoneal Fluid From Asymptomatic Infertile Womenm" Archives of Medical Research, 30: 138-143, 1999.

Hart et al., "Differential responses of human monocytes and macrophages to IL-4 and IL-13," Journal of Leukocyte Biology, 66: 575-578, 1999.

Bennett et al., "First-Trimester Human Chorionic Villi Express Both Immunoregulatory and Inflammatory Cytokines: A Role for Interleukin-10 in Regulating the Cytokine Network of Pregnancy," AJRI, 41: 70-78, 1999.

Ajjan et al., "Detection of IL-12, IL-13, and IL-15 Messenger Ribonucleic Acid in the Thyroid of Patients with Autoimmune Thyroid Disease," Journal of Clinical Endocrinology and Metabolism, 82: 666-669, 1997.

DETECTING AND TREATING REPRODUCTIVE TRACT DISORDERS

CROSS-REFERENCE TO RELATED APPLICATIONS

This application claims priority from U.S. provisional patent application Ser. No. 60/306,133 filed Jul. 17, 2001.

FIELD OF THE INVENTION

This invention relates generally to the fields of medicine and biotechnology. More particularly, the invention relates to methods of detecting and treating disorders of the female reproductive tract.

BACKGROUND

Recurrent spontaneous abortion (RSA) and endometriosis are female reproductive tract disorders that can lead to infertility and/or the inability of a woman to carry a fetus to term. RSA is defined as a condition in which a woman suffers from three or more consecutive spontaneous miscarriages. The etiology of this condition is poorly understood, but it has been linked to genetic, hormonal, anatomic, and/or immunologic anomalies and infection.

More information is known about endometriosis, a pathology characterized by the presence and growth of ectopic endometrial tissue outside the uterine cavity. Endometriosis is thought to be caused by retrograde menstruation, a process in which endometrial fragments are transported into the pelvis. Implantation and proliferation of such tissue fragments at ectopic sites can lead to pelvic pain, dyspareunia and even infertility. About 10% of reproductive age women suffer from endometriosis, and 30 to 40% of these experience infertility. Syrop C. H. and J. Halme, In: Wallach E. E., Kempers R. D., eds. Modern trends in infertility and contraception control. Boca Raton (Fla.), Year Book Medical Publishers, Inc, 343–51, 1988.

Unfortunately, the pathophysiology of RSA and endometriosis is not well understood. One hypothesis is that an unfavorable environment created by an immune/inflammatory-related condition in the peritoneal cavity and/or reproductive tract (e.g., ovary, fallopian tube, and endometrium) contributes to these disorders. Exposure of gametes to such an environment then leads to failure in oocyte maturation, ovulation, fertilization, and early embryonic development. Thus, a more complete understanding of the molecular and cellular events that underlie the pathophysiology of the female reproductive tract should lead to better methods for detecting, preventing, and treating disorders such as endometriosis and RSA.

SUMMARY

What has been discovered is that interleukin (IL)-13 and -15 (IL-13 and IL-15) are expressed at higher levels in both (a) endometria of women suffering from RSA and (b) endometrial implants from women suffering from endometriosis, than in the endometria of normal fertile women. Based on this discovery, it is believed that women having endometrial tissue exhibiting higher basal expression of IL-13 and IL-15 may be predisposed to developing RSA, endometriosis, peritoneal adhesions, and other disorders of the reproductive tract. It is also believed that increased levels of IL-13 and/or IL-15 may directly contribute to such pathologies.

Accordingly, the invention features a method for detecting a female reproductive tract disorder in a subject. This method includes the steps of: (a) providing a biological sample derived from the subject, e.g., endometrium or peritoneal fluid; (b) analyzing the expression of a cytokine such as IL-13 or IL-15 in the sample; and (c) correlating the expression of the cytokine with the presence or absence of the female reproductive tract disorder in the subject. Examples of reproductive tract disorders included endometriosis, RSA, and adhesion formation.

The step of analyzing expression of the cytokine can be performed by quantifying the amount of IL-13 and/or IL-15 present in the sample, e.g., by contacting the sample with an antibody that specifically binds IL-13 or IL-15. This step can also be performed by quantifying the amount of a nucleic acid that encodes IL-13 or IL-15 present in the sample, e.g., by contacting the sample with a polynucleotide that hybridizes under stringent conditions to the nucleic acid that encodes IL-13 or IL-15. The latter can also be performed using a polymerase chain reaction (PCR).

In some cases, expression of both IL-13 and IL-15 can be analyzed. In this case, step (c) of correlating the expression of the cytokine with the presence or absence of the female reproductive tract disorder in the subject can include determining the ratio of IL-13:IL-15 in the sample.

In another aspect, the invention features a method for modulating cytokine expression in female reproductive tract tissue. This method includes contacting the tissue with an agent that modulates expression of IL-13 and/or IL-15 in the tissue. The female reproductive tract tissue can be from a subject with endometriosis, RSA, and/or adhesion formation. The agent can be one that specifically binds IL-13 or IL-15, e.g., an antibody that specifically binds IL-13 or IL-15. The agent can also be a nucleic acid that modulates (i.e., increases or decreases) expression of IL-13 and/or IL-15 in a cell. The agent can also be one that modulates transcription or translation of a nucleic acid encoding IL-13 or IL-15. Thus, the agent can take the form of a polynucleotide such as an antisense oligonucleotide. In other variations of this method, the agent can be an ovarian steroid such as estradiol and medroxyprogesterone actetate.

As used herein, "bind," "binds," or "interacts with" means that one molecule recognizes and adheres to a particular second molecule in a sample, but does not substantially recognize or adhere to other structurally unrelated molecules in the sample. Generally, a first molecule that "specifically binds" a second molecule has a binding affinity greater than about $10^5$ to $10^6$ moles/liter for that second molecule.

By reference to an "antibody that specifically binds" another molecule is meant an antibody that binds the other molecule, and displays no substantial binding to other naturally occurring proteins other than those sharing the same antigenic determinants as other molecule. The term "antibody" includes polyclonal and monoclonal antibodies as well as antibody fragments or portions of immunolglobulin molecules that can specifically bind the same antigen as the intact antibody molecule.

As used herein, a "nucleic acid," "nucleic acid molecule," "oligonucleotide," or "polynucleotide" means a chain of two or more nucleotides such as RNA (ribonucleic acid) and DNA (deoxyribonucleic acid).

When referring to hybridization of one nucleic acid to another, "low stringency conditions" means in 10% formamide, 5× Denhart's solution, 6×SSPE, 0.2% SDS at 42° C., followed by washing in 1×SSPE, 0.2% SDS, at 50° C.; "moderate stringency conditions" means in 50% formamide, 5× Denhart's solution, 5×SSPE, 0.2% SDS at 42° C., followed by washing in 0.2×SSPE, 0.2% SDS, at 65° C.; and "high stringency conditions" means in 50% formamide, 5× Denhart's solution, 5×SSPE, 0.2% SDS at 42° C., followed by washing in 0.1×SSPE, and 0.1% SDS at 65° C. The phrase "under stringent conditions" means under low, moderate, or high stringency conditions.

The term "subject," as used herein, means a human or non-human animal, including but not limited to mammals such as a dog, cat, horse, cow, pig, sheep, goat, chicken, primate, rat, and mouse.

When referring to a cytokine, the phrase "modulates the expression of" means upregulates or downregulates the amount or functional activity of the cytokine, or otherwise modifies the availability of the cytokine to interact with a receptor.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including any definitions will control. In addition, the particular embodiments discussed below are illustrative only and not intended to be limiting.

Other features and advantages of the invention will be apparent from the following detailed description, and from the claims.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

Figure 1A:
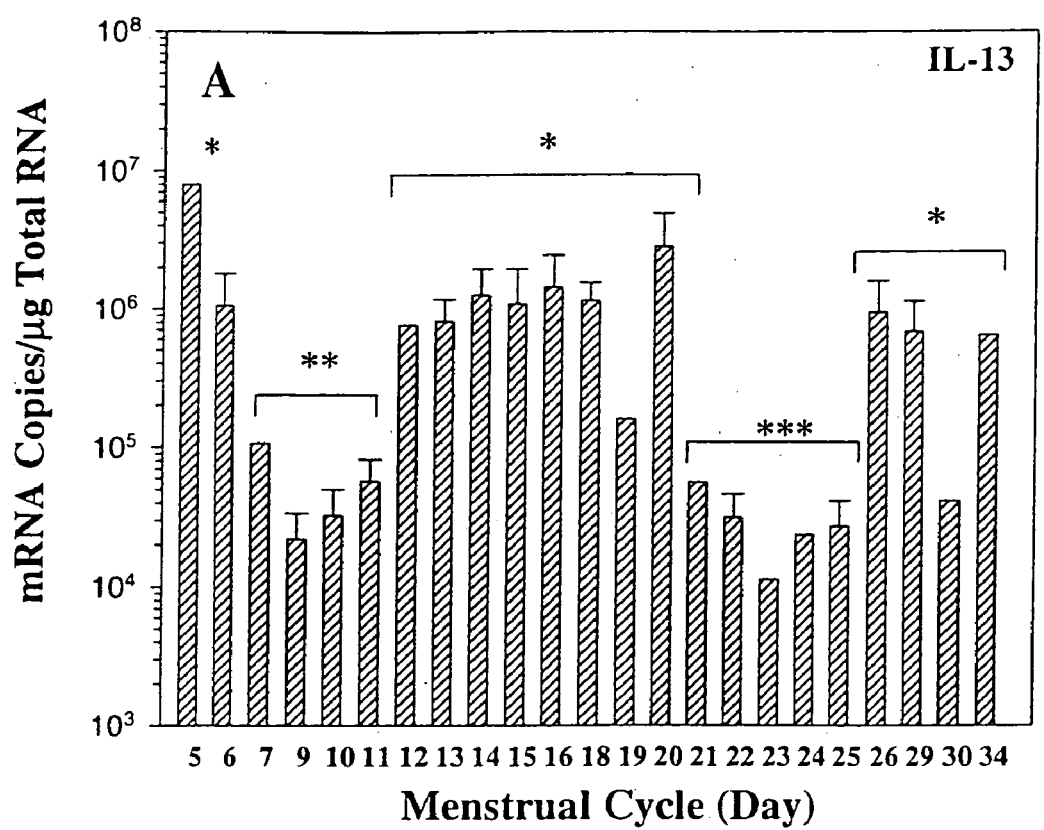
FIG. 1 is two bar graphs that show the mean±SEM copies of IL-13 (A) and IL-15 (B) mRNA expression/µg total RNA in normal endometrial biopsies taken throughout the menstrual cycle.

The invention provides methods and compositions for diagnosing, treating, preventing, and determining the predisposition of a subject to developing a disorder of the female reproductive tract such as endometriosis and RSA. In experiments leading to the development of the present invention, the expression of IL-13 and IL-15 was investigated in normal endometria, endometriosis implants, and endometria from subjects suffering from RSA.

IL-13 and IL-15

IL-13 and IL-15 are cytokines known to have functions similar to those ascribed to IL-4 and IL-2, respectively (Chomarat P. and J. Bannchereau, Int. Rev. Immunol. 17:1–52, 1998; Waldmann T. A. and Y. Tagaya, Ann. Rev. Immunol. 17:19–49, 1999). IL-13 has approximately 25% homology with IL-4, which is produced by T cells, mast cells and activated basophils, and regulates B-cell proliferation, IgG, IgE and MHC class II antigen expression and inhibits cytokine production by Th1 cells (Chomarat P. and J. Bannchereau, Int. Rev. Immunol. 17:1–52, 1998). IL-13 has been found to inhibit LPS-induced IL-1β and TNF-α expression in mice and, under in vitro conditions to suppress IL-1β and TNF-α production while promoting anti-inflammatory substances such as IL-1 receptor antagonist and IL-1 type II receptor (Chomarat P. and J. Bannchereau, Int. Rev. Immunol. 17:1–52, 1998; de Waal Malefyt R. et al., J. Immunol. 151: 6370–6381,1993; Di Santo E. et al., J. Immunol. 159:379–382,1997; Hart et al., J. Leukoc. Biol. 66:575–578, 1999; Muchamuel T. et al., J. Immunol. 158: 2898–2903,1997; Mijatovic et al., J. Biol. Chem. 272: 14394–14398, 1997). IL-13 mediates its biological activity through receptor components that are shared with IL-4, the IL-4Rα, as well as IL-13α1, IL-13α2 and the common γ receptors (Chomarat P. and J. Bannchereau, Int. Rev. Immunol. 17:1–52, 1998; Jensen P. L., Stem Cells 18:61–62, 2000; Murata T. et al., Int. J. Hematol. 69:13–20, 1999).

IL-15 is a pleiotrophic cytokine that is produced by a wide variety of tissues and cells, in particular by monocytes/macrophages, and mediates its biological activities through interaction with β and γ-chains of the IL-2 receptor and its own unique α chain (Waldman T. A. and Tagaya Y., Ann. Rev. Immunol. 17:19–49,1999; Fehniger T. A. and M. A. Caligiuri, Blood 97:14–32, 2001). Macrophage-derived IL-15 is reported to induce a local innate tissue inflammatory infiltrate, particularly in response to infection and to act as a key component of the adaptive immune response (Waldman T. A. and Tagaya Y., Ann. Rev. Immunol. 17:19–49, 1999; Fehniger T. A. and M. A. Caligiuri, Blood 97:14–32, 2001)). IL-15 regulates NK cell proliferation, cytotoxicity, and also, through synergistic interaction with IL-2, stimulates the production of IFN-β and TNF-α (Waldman T. A. and Tagaya Y., Ann. Rev. Immunol. 17:19–49, 1999; Bulfone-Paus S. et al., FASEB J. 13:1575–1585, 1999; Marks-Konczalik J. et al., Arch. Med. Res. 30:138–143, 1999). Co-culturing of macrophages with NK cells has been shown to result in abundant production of IFN-γ following LPS stimulation that required IL-15 expression (Fehniger T. A. and M. A. Caligiuri, Blood 97:14–32, 2001).

Expression of IL-13 and IL-15 in Reproductive Tract Disorders

In studies described herein, evidence was obtained that IL-13 and IL-15 mRNA and protein are expressed in normal endometrium throughout the menstrual cycle and RSA during days 7–9 post-LH surge (cycle days 21–23). In normal endometrium peak expression for both cytokines was detected immediately after and prior to the onset of menses, and in two distinct periods corresponding to the late proliferative phase for IL-13, and early-mid secretory phases for IL-15. The patterns of endometrial IL-13 and IL-15 protein production were similar to the corresponding mRNA expression patterns, with the exception of lower IL-13 production during the secretory phase. The ratios of IL-13:IL-15 mRNA and protein expression at different stages of the cycle revealed a predominance in IL-13 expression during late proliferative/early secretory phase, and a predominance of IL-15 mRNA, but not protein expression, during the mid secretory phase. In comparison with normal samples, the endometria from women with RSA expressed elevated levels of IL-13 and IL-15 mRNA and protein, with the IL-13: IL-15 ratio favoring IL-13. Compared to periods of their peak expression and days 21–23 of the normal menstrual cycle, the ratio of IL-13 and IL-15 mRNA and protein in normal:RSA further revealed their elevated expression in endometrium of women with RSA.

Immunoreactive proteins were localized primarily in normal endometrial luminal epithelial cells. Increased intensity of immunostaining was observed in glandular epithelial and stromal cells in RSA. Taken together these results provide evidence that endometrium of normal fertile women expresses IL-13 and IL-15 with two distinct profiles during the menstrual cycle coinciding with local endometrial inflammatory/immune responses, tissue repair and embryo implantation. Importantly, IL-13 and IL-15 show elevated expression in women with RSA.

In other experiments, IL-13 and IL-15 mRNA and protein expression were determined in ectopic and matched eutopic endometrium, and endometrium of normal fertile women, as well as in peritoneal fluids of patients with and without endometriosis, and in women with peritoneal adhesions unrelated to endometriosis. Using quantitative RT-PCR and ELISA, it was found that ectopic and eutopic endometrium analyzed during proliferative and secretory phases of the menstrual cycle expressed IL-13 and IL-15 mRNA and protein, with higher levels of mRNA expression in ectopic compared to eutopic and normal endometrium irrespective of the phase of the menstrual cycle. IL-13 and IL-15 protein content in ectopic, but not eutopic endometrium was significantly higher than normal. The ratio of IL-13:IL-15 in ectopic, eutopic and normal endometrium and their ratios in ectopic:eutopic, ectopic:normal and eutopic:normal endometrium further indicated that IL-13 and IL-15 are expressed at elevated levels in ectopic tissue, with a higher ratio in ectopic and eutopic, compared to normal endometrium.

IL-13 and IL-15 content in the peritoneal fluid (PF) of women with endometriosis was also higher, but not significantly different compared to women with adhesions and normal pelvic anatomy, with the exception of IL-13 in adhesion and IL-15 in endometriosis. Results of immunohistochemical staining of IL-13 and IL-15 in ectopic endometrium showed that luminal/glandular epithelial cells and immune/inflammatory cells present within the stromal compartment of the ectopic endometrium were the primarily site of IL-13 and IL-15 expression and presented with less intensity in eutopic and normal endometrium.

Methods

Methods involving conventional molecular biology techniques are described herein. Such techniques are generally known in the art and are described in detail in methodology treatises such as Molecular Cloning: A Laboratory Manual, 2nd ed., vol. 1–3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Various techniques using polymerase chain reaction (PCR) are described, e.g., in Innis et al., PCR Protocols: A Guide to Methods and Applications, Academic Press: San Diego, 1990. Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

Detecting Reproductive Tract Disorders

Based on the foregoing discoveries, the invention provide a method for detecting a female reproductive tract disorder in a subject. This method includes the steps of: (a) providing a biological sample derived from the subject, e.g., endometrium or peritoneal fluid; (b) analyzing the expression of a cytokine such as IL-13 or IL-15 in the sample; and (c) correlating the expression of the cytokine with the presence or absence of the female reproductive tract disorder in the subject.

Suitable subjects for use in the invention can be any animal having a female reproductive tract or peritoneum. For example, the subject can be a female animal such as mammal like a dog, cat, horse, cow, pig, sheep, goat, chicken, primate, rat, or mouse. Because the experiments presented herein relate to human subjects, a preferred subject for the methods of the invention is a human female. Particularly preferred are subjects suspected of having or at risk for developing a reproductive tract disorder, e.g., a woman suspected of having or at risk for developing endometriosis, RSA, or peritoneal adhesions based on clinical findings or other diagnostic test results.

The step of providing a biological sample derived from the subject can be performed by conventional medical techniques. For example, an endometrial tissue sample can be taken from the subject by biopsy. As another example, a sample of peritoneal fluid can be taken from a subject by conventional techniques. Suitable methods are described in more detail in the Examples sections presented below.

The step of analyzing the expression of a cytokine such as IL-13 or IL-15 in the sample can be performed in a variety of different ways. Numerous suitable techniques are known for analyzing cytokine expression. For example, cytokine expression can be determined directly by assessing protein expression of cells or fluid of a biological sample (e.g., endometrial tissue or peritoneal fluid). Protein expression can be detected using immunological techniques, e.g., using antibodies that specifically bind the protein (e.g., IL-13 or IL-15) in assays such as immunofluorescence or immunohistochemical staining and analysis, enzyme-linked immunosorbent assay (ELISA), radioimmunoassay (RIA), immunoblotting (e.g., Western blotting), and like techniques. Expression of IL-13 and/or IL-15 can also be determined by directly or indirectly measuring the amount of mRNA encoding IL-13 or IL-15 in a cellular sample using known techniques such as Northern blotting and PCR-based methods such as competitive quantitative reverse transcriptase PCR (Q-RT-PCR). Suitable methods for analyzing expression of IL-13 or IL-15 are described below; nonetheless, other suitable methods might also be employed.

The step of correlating the expression of the cytokine with the presence or absence of the female reproductive tract disorder in the subject involves comparing the level of cytokine expression in the test biological sample with levels of cytokines expressed in control samples, e.g., those derived from subjects known to have or not to have the particular disorder. Thus, after quantifying IL-13 and/or IL-15 expression in a biological sample from a test subject, the test result is compared to levels of IL-13 and/or IL-15 expression determined from (a) a panel of tissues derived from subjects (preferably matched to the test subject by age, species, strain or ethnicity, and/or other medically relevant criteria) known to have a particular disorder and (b) a panel of tissues derived from subjects (preferably also matched as above) known not to have a particular disorder. If the test result is closer to the levels (e.g., mean or arithmetic average) from the panel of tissues derived from subjects known to have a particular disorder, then the test result correlates with the test subject having the particular disorder. On the other hand, if the test result is closer to the levels (e.g., mean or arithmetic average) from the panel of tissues derived from subjects known not to have a particular disorder, then the test result correlates with the test subject not having the particular disorder.

Modulating Cytokine Expression

The invention also provides a method for modulating cytokine expression in female reproductive tract tissue. Restoration of cytokine expression to levels associated with normal reproductive tract tissue is expected to ameliorate at least some of the symptoms of the reproductive tract disorder. This method includes the step of contacting the tissue with an agent that modulates expression of IL-13 and/or IL-15 in the tissue.

The tissue for use in this method can be any derived from a female reproductive system, e.g., endometrium, or tissue derived from the uterus, cervix, vagina, fallopian tube, or ovary. The tissue can be from any animal having a female reproductive tract, e.g., a mammal like a dog, cat, horse, cow, pig, sheep, goat, chicken, primate, rat, or mouse. Because the experiments presented herein relate to human subjects, a preferred tissue sample for the methods of the invention is one derived from a human female. Particularly preferred is tissue derived from a subject suspected of having or at risk for developing a reproductive tract disorder, e.g., a woman suspected of having or at risk for developing endometriosis, RSA, or peritoneal adhesions based on clinical findings or other diagnostic test results.

The method utilizes an agent that modulates expression of IL-13 and/or IL-15 in the tissue. Numerous agents for modulating expression of a cytokine in a tissue are known. Any of these suitable for the particular system being used may be employed. Typical agents for modulating expression of a cytokine are proteins, nucleic acids, and small organic or inorganic molecules such as hormones (e.g., natural or synthetic steroids).

An example of a protein that can modulate IL-13 or IL-15 expression is an antibody that specifically binds IL-13 or IL-15. Such an antibody can be used to interfere with the interaction of IL-13 or IL-15 protein and other molecules that bind IL-13 or IL-15 protein. IL-13 or IL-15 proteins (or immunogenic fragments or analogs thereof) can be used to raise antibodies useful in the invention. Such proteins can be produced by purification from cells/tissues, recombinant techniques or chemical synthesis as described above. Antibodies for use in the invention include polyclonal antibodies, monoclonal antibodies, single chain antibodies, Fab fragments, F(ab')$_2$ fragments, and molecules produced using a Fab expression library. See, for example, Kohler et al., Nature 256:495, 1975; Kohler et al., Eur. J. Immunol. 6:511, 1976; Kohler et al., Eur. J. Immunol. 6:292, 1976; Hammerling et al., "Monoclonal Antibodies and T Cell Hybridomas," Elsevier, N.Y., 1981; Ausubel et al., supra; U.S. Pat. Nos. 4,376,110, 4,704,692, and 4,946,778; Kosbor et al., Immunology Today 4:72, 1983; Cole et al., Proc. Natl. Acad. Sci. USA 80:2026, 1983; Cole et al., "Monoclonal Antibodies and Cancer Therapy," Alan R. Liss, Inc., pp. 77–96, 1983; and Huse et al., Science 246:1275, 1989.

Other proteins that can modulate IL-13 or IL-15 expression include IL-13 or IL-15 protein variants that can compete with native IL-13 or native IL-15 for binding ligands such as naturally occurring receptors of these cytokines. Such protein variants can be generated through various techniques known in the art. For example, IL-13 or IL-15 protein variants can be made by mutagenesis, such as by introducing discrete point mutation(s), or by truncation. Mutation can give rise to a IL-13 or IL-15 protein variant having substantially the same, or merely a subset of the functional activity of a native IL-13 or IL-15 protein. Alternatively, antagonistic forms of the protein can be generated which are able to inhibit the function of the naturally occurring form of the protein, such as by competitively binding to another molecule that interacts with IL-13 or IL-15 protein. In addition, agonistic (or superagonistic) forms of the protein may be generated that constitutively express one or more IL-13 or IL-15 functional activities. Other variants of IL-13 or IL-15 proteins that can be generated include those that are resistant to proteolytic cleavage, as for example, due to mutations which alter protease target sequences. Whether a change in the amino acid sequence of a peptide results in an IL-13 or IL-15 protein variant having one or more functional activities of a native IL-13 or IL-15 protein can be readily determined by testing the variant for a native IL-13 or IL-15 protein functional activity (e.g., binding a receptor or inducing a cellular response).

Another agent that can modulate IL-13 or IL-15 expression is an IL-13 or IL-15 non-peptide mimetic or chemically modified form of IL-13 or IL-15 that disrupts binding of an IL-13 or IL-15 protein to other proteins or molecules with which the native IL-13 or IL-15 protein interacts. See, e.g., Freidinger et al. in Peptides: Chemistry and Biology, G. R.

Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopepitides (Ewenson et al. (1986) J. Med. Chem. 29:295; and Ewenson et al. in Peptides: Structure and Function (Proceedings of the 9th American Peptide Symposium) Pierce Chemical Co. Rockland, Ill., 1985), beta-turn dipeptide cores (Nagai et al. (1985) Tetrahedron Lett 26:647; and Sato et al. (1986) J. Chem. Soc. Perkin. Trans. 1:1231), and beta-aminoalcohols (Gordon et al. (1985) Biochem. Biophys. Res. Commun. 126:419; and Dann et al. (1986) Biochem. Biophys. Res. Commun. 134:71). IL-13 or IL-15 proteins may also be chemically modified to create IL-13 or IL-15 protein derivatives by forming covalent or aggregate conjugates with other chemical moieties, such as glycosyl groups, lipids, phosphate, acetyl groups and the like. Covalent derivatives of IL-13 or IL-15 protein can be prepared by linking the chemical moieties to functional groups on amino acid side chains of the protein or at the N-terminus or at the C-terminus of the polypeptide.

The agent that directly reduces expression of the cytokine can also be a nucleic acid that reduces expression of IL-13 or IL-15. For example, the nucleic acid can be an antisense nucleic acid that hybridizes to mRNA encoding IL-13 or IL-15. Antisense nucleic acid molecules for use within the invention are those that specifically hybridize (e.g. bind) under cellular conditions to cellular mRNA and/or genomic DNA encoding an IL-13 or IL-15 protein in a manner that inhibits expression of the IL-13 or IL-15 protein, e.g., by inhibiting transcription and/or translation. The binding may be by conventional base pair complementarity, or, for example, in the case of binding to DNA duplexes, through specific interactions in the major groove of the double helix.

Antisense constructs can be delivered as an expression plasmid which, when transcribed in the cell, produces RNA which is complementary to at least a unique portion of the cellular mRNA which encodes an IL-13 or IL-15 protein. Alternatively, the antisense construct can take the form of an oligonucleotide probe generated ex vivo which, when introduced into an IL-13 or IL-15 protein expressing cell, causes inhibition of IL-13 or IL-15 protein expression by hybridizing with an mRNA and/or genomic sequences coding for IL-13 or IL-15 protein. Such oligonucleotide probes are preferably modified oligonucleotides that are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see, e.g., U.S. Pat. Nos. 5,176,996; 5,264,564; and 5,256,775). Additionally, general approaches to constructing oligomers useful in antisense therapy have been reviewed, for example, by Van der Krol et al., Biotechniques 6:958–976, 1988; and Stein et al., Cancer Res. 48:2659–2668, 1988. With respect to antisense DNA, oligodeoxyribonucleotides derived from the translation initiation site, e.g., between the −10 and +10 regions of an IL-13 or IL-15 protein encoding nucleotide sequence, are preferred.

Antisense approaches involve the design of oligonucleotides (either DNA or RNA) that are complementary to IL-13 or IL-15 mRNA. The antisense oligonucleotides will bind to IL-13 or IL-15 mRNA transcripts and prevent translation. Absolute complementarity, although preferred, is not required. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. (Wagner, R., Nature 372:333, 1994). Therefore, oligonucleotides complementary to either the 5' or 3' untranslated, non-coding regions of an IL-13 or IL-15 gene could be used in an antisense approach to inhibit translation of endogenous IL-13 or IL-15 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of IL-13 or IL-15 mRNA, antisense nucleic acids should be at least eighteen nucleotides in length, and are preferably less than about 100 and more preferably less than about 30, 25, 20, or 18 nucleotides in length.

Antisense oligonucleotides of the invention may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxyethyl)uracil, 5-carboxymethylaminomethyl-2-thiouridine, 5-carboxymethylaminomethyluracil, dihydrouricil, beta-D-galactosylqueosine, inosine, N6-isopentenyladenine, 1-methylguanine, 1-methylinosine, 2,2-idimethylguanine, 2-methyladenine, 2-methylguanine, 3-methylcytosine, 5-methylcytosine, N6-adenine, 7-methylguanine, 5-methylaminomethyluracil 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Antisense oligonucleotides of the invention may also comprise at least one modified sugar moiety selected from the group including but not limited to arabinose, 2-fluoroarabinose, xylulose, and hexose; and may additionally include at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., Nucl. Acids Res. 15:6625–6641, 1987). Such oligonucleotide can be a 2'-O-methylribonucleotide (Inoue et al., Nucl. Acids Res. 15:6131–6148, 1987), or a chimeric RNA-DNA analogue (Inoue et al., FEBS Lett. 215:327–330, 1987).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209), methylphosphonate oligonucleotides can be prepared by use of controlled pore glass polymer supports (Sarin et al., Proc. Natl. Acad. Sci. U.S.A. 85:7448–7451, 1988).

The antisense molecules should be delivered into cells that express IL-13 or IL-15 in vivo. A number of methods have been developed for delivering antisense DNA or RNA into cells. For instance, antisense molecules can be introduced directly into the tissue site by such standard techniques as electroporation, liposome-mediated transfection, CaCl-mediated transfection, or the use of a gene gun. Alternatively, modified antisense molecules, designed to target the desired cells (e.g., antisense linked to peptides or antibodies that specifically bind receptors or antigens expressed on the target cell surface) can be used.

However, because it is often difficult to achieve intracellular concentrations of the antisense sufficient to suppress translation of endogenous mRNAs, a preferred approach utilizes a recombinant DNA construct in which the antisense oligonucleotide is placed under the control of a strong promoter (e.g., the CMV promoter). The use of such a construct to transform cells will result in the transcription of sufficient amounts of single stranded RNAs that will form complementary base pairs with the endogenous IL-13 or IL-15 transcripts and thereby prevent translation of IL-13 or IL-15 mRNA.

Ribozyme molecules designed to catalytically cleave IL-13 or IL-15 mRNA transcripts can also be used to prevent translation of IL-13 or IL-15 mRNA and expression of IL-13 or IL-15 protein (see, e.g., PCT Publication No. WO 90/11364, published Oct. 4, 1990; Sarver et al., Science 247:1222–1225, 1990 and U.S. Pat. No. 5,093,246). While ribozymes that cleave mRNA at site specific recognition sequences can be used to destroy IL-13 or IL-15 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591, 1988. Preferably the ribozyme is engineered so that the cleavage recognition site is located near the 5' end of IL-13 or IL-15 mRNA; i.e., to increase efficiency and minimize the intracellular accumulation of non-functional mRNA transcripts. Ribozymes within the invention can be delivered to a cell using a vector.

Endogenous IL-13 or IL-15 gene expression can also be reduced by inactivating or "knocking out" the IL-13 or IL-15 gene or its promoter using targeted homologous recombination. See, e.g, Kempin et al., Nature 389: 802 (1997); Smithies et al., Nature 317:230–234, 1985; Thomas and Capecchi, Cell 51:503–512, 1987; and Thompson et al., Cell 5:313–321, 1989. For example, a mutant, non-functional IL-13 or IL-15 gene variant (or a completely unrelated DNA sequence) flanked by DNA homologous to the endogenous IL-13 or IL-15 gene (either the coding regions or regulatory regions of the IL-13 or IL-15 gene) can be used, with or without a selectable marker and/or a negative selectable marker, to transfect cells that express IL-13 or IL-15 protein in vivo.

Alternatively, endogenous IL-13 or IL-15 gene expression might be reduced by targeting deoxyribonucleotide sequences complementary to the regulatory region of the IL-13 or IL-15 gene (i.e., the IL-13 or IL-15 promoter and/or enhancers) to form triple helical structures that prevent transcription of the IL-13 or IL-15 gene in target cells. (See generally, Helene, C.,Anticancer Drug Des. 6(6):569–84, 1991; Helene, C., et al., Ann. N.Y. Acad. Sci. 660:27–36, 1992; and Maher, L. J., Bioassays 14(12):807–15, 1992).

Antisense nucleic acid, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramide chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters. Alternatively, antisense cDNA constructs that synthesize antisense RNA constitutively or inducibly, depending on the promoter used, can be introduced stably into cell lines.

Another agent that can be used to modulate cytokine expression in female reproductive tract tissue is a hormone. Numerous naturally occurring and synthetic hormones are known to cause physiological changes in such tissue and are available commercially. See, e.g., *PDR: Physician's Desk Reference*, 2002. Those particular hormones which modulate IL-13 or IL-15 expression in a given sample tissue can be determined empirically by contacting a series of tissue samples with a panel of different hormones and analyzing the tissue samples for changes in phenotype over time. In experiments relating to the invention, it was shown that ovarian steroids such as estradiol and medroxyprogesterone acetate can modulate IL-13 and IL-15 expression in endometrial epithelial and stromal cells at both the mRNA and protein level. Such ovarian steroids were also shown to modulate the IL-13 and IL-15 effect (i.e., DNA synthesis and cell proliferation) on endometrial epithelial and stromal cells.

The agent that can be used to modulate cytokine expression in female reproductive tract tissue may be administered to non-human animals or humans in pharmaceutically acceptable carriers (e.g., physiological saline), that are selected on the basis of mode and route of administration and standard pharmaceutical practice. For example, the pharmaceutical compositions of the invention might include suitable buffering agents such as acetic acid or its salt (1–2% w/v); citric acid or its salt (1–3% w/v); boric acid or its salt (0.5–2.5% w/v); succinic acid; or phosphoric acid or its salt (0.8–2% w/v); and suitable preservatives such as benzalkonium chloride (0.003–0.03% w/v); chlorobutanol (0.3–0.9% w/v); parabens (0.01–0.25% w/v) or thimerosal (0.004–0.02% w/v). Examples of compositions suitable for parenteral administration include sterile aqueous preparations such as water, Ringer's solution, and isotonic sodium chloride solution. In addition, sterile, fixed oils might be used as a solvent or suspending medium. For this purpose, any bland fixed oil may be employed including synthetic mono-or di-glycerides. In addition, fatty acids such as oleic acid find use in the preparation of injectables. Carrier formulations suitable for local, subcutaneous, intramuscular, intraperitoneal or intravenous administrations may be found in Remington's Pharmaceutical Sciences, Mack Publishing Company, Easton, Pa. The pharmaceutical compositions useful in the invention may be delivered in mixtures of more than one pharmaceutical composition.

The compositions of the invention may be administered to animals or humans by any conventional technique. Such administration might be parenteral (e.g., intravenous, subcutaneous, intramuscular, or intraperitoneal introduction). Preferably, the compositions may also be administered directly to the target site (e.g., a portion of the reproductive tract or peritoneal cavity) by, for example, surgical delivery to an internal or external target site, or by catheter to a site accessible by a blood vessel. Other methods of delivery, e.g., liposomal delivery or diffusion from a device impregnated with the composition, are known in the art. The composition may be administered in a single bolus, multiple injections, or by continuous infusion (e.g., intravenously or by peritoneal dialysis).

The methods of this invention, generally speaking, may be practiced using any mode of administration that is medically acceptable, meaning any mode that produces effective levels of response without causing clinically unacceptable adverse effects. Preferred modes of administration include parenteral, injection, infusion, deposition, implantation, anal or vaginal supposition, oral ingestion, inhalation, and topical administration. Injections can be intravenous, intradermal, subcutaneous, intramuscular, or interperitoneal. For example, the pharmaceutical composition can be injected directly into target site in the reproductive tract for the prevention of endometriosis, RSA, or adhesion formation. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially fused pellets. Inhalation includes administering the pharmaceutical composition with an aerosol in an inhaler, either alone or attached to a carrier that can be absorbed. For systemic administration, it may be preferred that the pharmaceutical composition is encapsulated in liposomes. The term "parenteral" includes subcutaneous injections, intravenous, intramuscular, intraperitoneal, intrastemal injection or infusion techniques. In certain preferred embodiments of the invention, the administration can be designed so as to result in sequential exposure of the pharmaceutical composition over some period of time, e.g., hours, days, weeks, months or years. This can be accomplished by repeated administrations of the pharmaceutical composition, by one of the methods described above, or alternatively, by a sustained-release delivery system in which the pharmaceutical composition is delivered to the subject for a prolonged period without repeated administrations. By sustained-release delivery system, it is meant that total release of the pharmaceutical composition does not occur immediately upon administration, but rather is delayed for some period of time. Release can occur in bursts or it can occur gradually and continuously. Administration of such a system can be, e.g., by long-lasting oral dosage forms, bolus injections, transdermal patches, and subcutaneous implants.

A therapeutically effective amount is an amount which is capable of producing a medically desirable result in a treated animal or human. As is well known in the medical arts, dosage for any one animal or human depends on many factors, including the subject's size, body surface area, age, the particular composition to be administered, sex, time and route of administration, general health, and other drugs being administered concurrently. Toxicity and therapeutic efficacy of the compositions of the invention can be determined by standard pharmaceutical procedures, using cells in culture and/or experimental animals to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Agents that exhibit large therapeutic indices are preferred. While agents that exhibit toxic side effects may be used, care should be taken to design a delivery system that targets such compounds to the site of the tissues to be treated in order to minimize potential damage to uninvolved tissue and thereby reduce side effects. The data obtained from cell culture assays and animal studies can be used in formulating a range of dosage for use in humans. The dosage of such compounds lies preferably within the range of circulating concentrations that include an ED50 with little or no toxicity. The dosage may vary within this range depending on the dosage form employed and the route of administration utilized.

EXAMPLES

The following examples serve to illustrate the invention without limiting it thereby. It will be understood that variations and modifications can be made without departing from the spirit and scope of the invention.

Example I

Differential Expression of IL-13 and IL-15 Throughout the Menstrual Cycle in Endometrium of Normal Fertile Women and Women with RSA Materials and Methods Sources of materials. All the materials for Q-RT-PCR, ELISA and immunohistochemistry were purchased from commercial sources as previously described in Chegini N. et al., Am. J. Reprod. Immunol. 42:297–302, 1999; and Zhao Y. and Chegini N., Am. J. Reprod. Immunol. 42:303–311, 1999). Endometrial biopsies from throughout the menstrual cycle were collected from women (N=49) with documented fertility using an endometrial sampling catheter (Pipelle™, Unimar Inc. Wilton, Conn.). Biopsies were also obtained at day 7 to 9 of post-LH surge (to rule out the possibility of luteal phase defect) from women (N=13) with a history of at least three spontaneous miscarriages of unknown etiology. All subjects gave informed consent to the collection of the biopsies, were of reproductive age, and were not taking any hormone therapy prior to the biopsies. Endometrial dating was determined by histological evaluation and the last menstrual period. The biopsies were divided into three portions and used for total RNA and protein isolation, and immunohistochemistry.

Expression of IL-13 and IL-15 mRNA. Total cellular RNA was isolated from endometrial biopsies and subjected to standard and competitive quantitative RT-PCR. The competitive Q-RT-PCR used an external synthetic cRNA standard prepared from a template plasmid constructed using overlapping oligonucleotides with complementary sequences to the 3', 5' and internal PCR primers of human ILs including IL-13 and IL-15 genes, as previously described (Chegini N. et al., Am. J. Reprod. Immunol. 42:297–302, 1999). Total cellular RNA (2 µg) and several dilutions of the cRNA standard ($10^3$–$10^8$ copies/reaction) were subjected to RT-PCR and co-amplified under a condition described previously for 35 cycles of 1.5 min at 94° C., 2 min at 58° C. and 3 min at 72° C. (Chegini N. et al., Am. J. Reprod. Immunol. 42:297–302, 1999). The PCR products were separated on agarose gels containing ethidium bromide, photographed using a Kodak 290 digital camera, and the images were stored as TIFF files (Chegini N. et al., Am. J. Reprod. Immunol. 42:297–302, 1999). The PCR product band intensities were determined using NIH-Image and following normalization for their molecular weight the ratio of the band intensity was plotted against the copy number of the cRNA/reaction. The final quantity of mRNA expression was derived from the plots where the ratio of cRNA/target mRNA is equal to 1 and reported as mean±SEM of mRNA copies/μg total RNA. The detailed procedure to calculate the final mRNA expression has been previously described (Chegini N. et al., Am. J. Reprod. Immunol. 42:297–302, 1999).

Enzyme-linked immunoassay (ELISA) of IL-13 and IL-15. To determine IL-13 and IL-15 protein content, endometrial biopsies were homogenized in buffer consisting of 25 mM Tris-HCl, pH (8.0), 1 mM EDTA, 150 mM NaCl, 1% triton X-100, 5 mM NaF and protease inhibitor cocktail. The homogenates were centrifuged at 10,000×g for 15 min at 4° C., the supernatants were collected, their total protein content determined using a conventional method (Pierce, Rockford, Ill.) and aliquots were stored at −80° C. until assayed. IL-13 and IL-15 content was determined using human specific IL-13 and IL-15 ELISA kits purchased from R & D Systems (Minneapolis, Minn.) with detection limits of 32 and 3 pg/ml, respectively.

Immunohistochemistry. The endometrial cellular distribution of IL-13 and IL-15 protein was determined by immunohistochemistry as previously described (Zhao Y. and Chegini N., Am. J. Reprod. Immunol. 42:303–311, 1999). Endometrial biopsies were fixed in Bouin's solution and embedded in paraffin. Tissue sections 3 to 5 μm were prepared. Following standard procedures, the sections were incubated with goat anti-human recombinant IL-13 polyclonal antibody (R & D Systems) and a monoclonal antibody generated against recombinant hIL-15 (Genzyme Co., Cambridge, MA) at 5 μg IgG/ml prepared in phosphate buffered saline, pH 7.4, containing 0.1% bovine serum albumin (Zhao Y. and Chegini N., Am. J. Reprod. Immunol. 42:303–311, 1999). The sections were then exposed to biotinylated secondary antibodies and avidin horseradish peroxidase. The chromogenic reaction was developed using 3,3'diaminobenzidine. Controls included incubation of tissue sections with mouse or goat IgG instead of the primary antibodies, and omission of the primary antibodies.

Statistical analyses. Statistical analysis was performed by unpaired Student t-test and Kruskal-Wallis one-way analysis of variance with Dunn test, using computer software program SigmaStat (Jandel Co, San Rafael, Calif.). A probability level of P<0.05 was considered significant.

Results

IL-13 and IL-15 mRNA expression in normal endometria. Standard and competitive Q-RT-PCR indicated that endometrium from normal fertile women throughout the menstrual cycle, and women with RSA from day 7–9 of LH surge (cycle day 21–23), expresses IL-13 and IL-15 mRNA. Quantitative analysis of IL-13 and IL-15 mRNA expression in normal endometrium revealed a significant variation in their expression throughout the menstrual cycle (FIGS. 1A and B).

Referring to FIG. 1A, the pattern of IL-13 mRNA expression showed several periods of peak expression occurring immediately after menses, during the mid-late proliferative and early secretory phases, and at the late secretory phase immediately before the onset of menses. There were also two periods of sharp decline in IL-13 mRNA expression that occurred during the early-mid proliferative and mid-late secretory phases, representing a reduction ranging from 10- to 20-fold from the peak values. The values were calculated from the band densities as described in materials and methods. Probabilities indicated by asterisks in FIG. 1A were as follows: * vs ** (P=0.003); * vs * (P=0.001 and 0.01); and  vs *** (P=0.3).

Figure 1B:
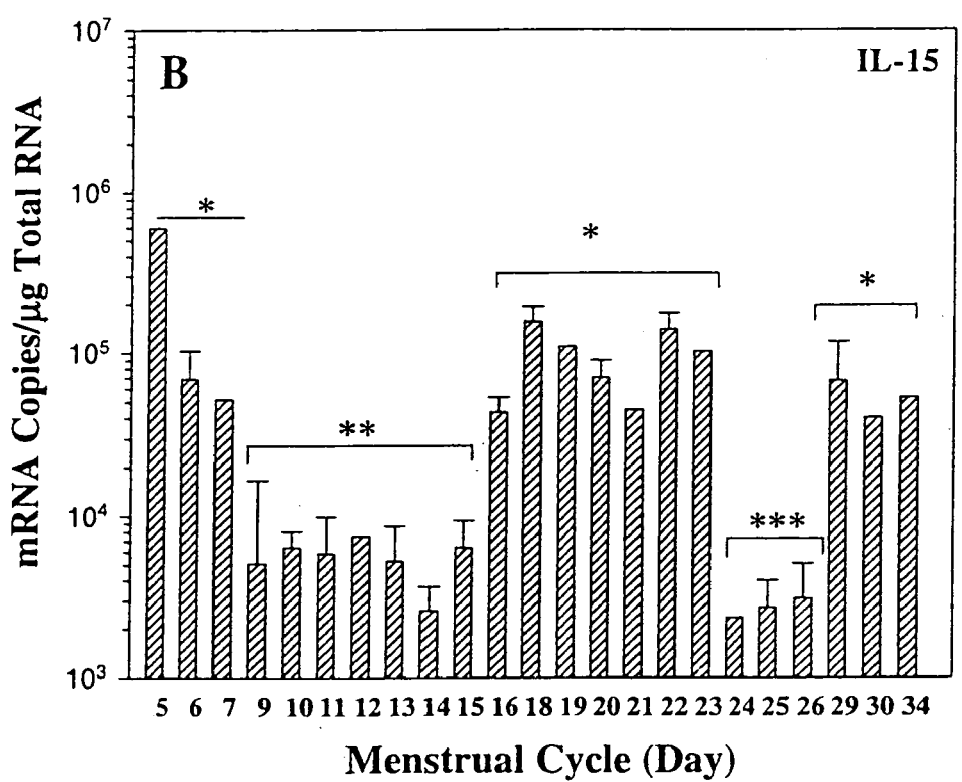

Referring to FIG. 1B, the endometrial pattern of IL-15 mRNA expression during the normal menstrual cycle also revealed several periods of peak expression, occurring immediately after menses, in early-mid secretory phase, and prior to the onset of menses, with two periods of decline that were observed during the proliferative and the late secretory phases. In FIG. 1B, statistical values were the following: * vs ** (P=0.001); * vs * (P=0.008); and  vs *** (P=0.02).

Figure 2:
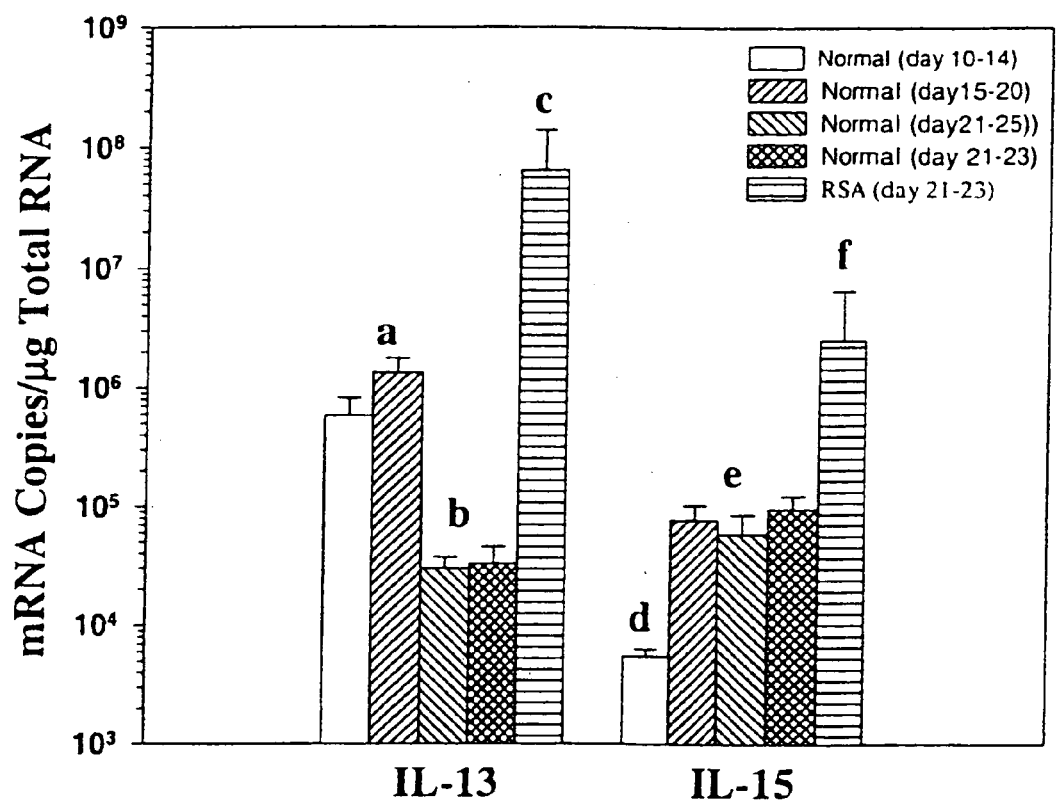
FIG. 2 is a bar graph that shows the mean±SEM copies of IL-13 and IL-15 mRNA expression/µg total RNA in endometria of normal fertile women at days 10–14, 15–20, 21–25 and 21–23 of the menstrual cycle and women with RSA at days 7–9 post luteinizing hormone (LH) surge (cycle days 21–23).

IL-13 and IL-15 mRNA expression in RSA. Referring now to FIG. 2, endometrial biopsies obtained from women with RSA (taken on day 7 and 9 post-LH surge; cycle days 21–23) expressed a significantly higher levels of both IL-13 and IL-15 mRNA than the respective peak expression levels detected in endometria of normal fertile women. The RSA values on cycle days 21–23 were significantly higher than normals at various stages, including late proliferative (cycle days 10–14), early secretory (cycle days 15–20), and mid secretory (cycle days 21–25) phases, as well as normal cycle days 21–23. Statistical differences for IL-13 were as follows: a differs from b (P=0.02) and from c (P=0.004); b differs from c (P=0.0001). For IL-15; d differs from e (P=0.05) and from f (P=0.0001); e differs from f (P=0.02); a differs from d and e (P=0.0001 and 0.03); b differs from f (P=0.02) and c differs from f (P=0.05).

Figure 3A:
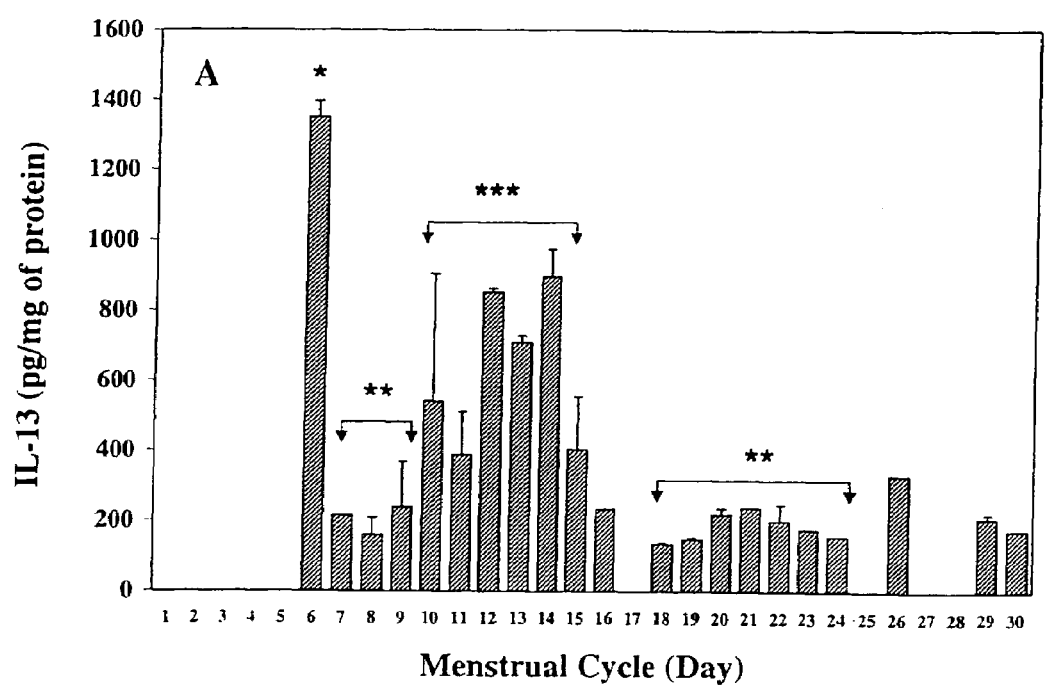
FIG. 3 is two bar graphs that show the mean±SEM level of IL-13 (A) and IL-15 (B) protein expression in normal endometrial biopsies taken throughout the menstrual cycle.

IL-13 and IL-15 protein expression in normal endometria. Results of the ELISA assays showed that endometrial biopsies of normal fertile women also expressed IL-13 and IL-15 protein, with significant fluctuation in levels throughout the menstrual cycle. Referring to FIGS. 3A and B, both cytokines showed a peak of expression immediately following menses, with a sharp decline during the early proliferative phase (P=0.02 for IL-13 and 0.03 for IL-15). Additionally, for IL-13, a period of peak production was observed during the mid-late proliferative phase. This was followed by a significant decline throughout the secretory phase (FIG. 3A; P=0.02 and 0.03).

Figure 3B:
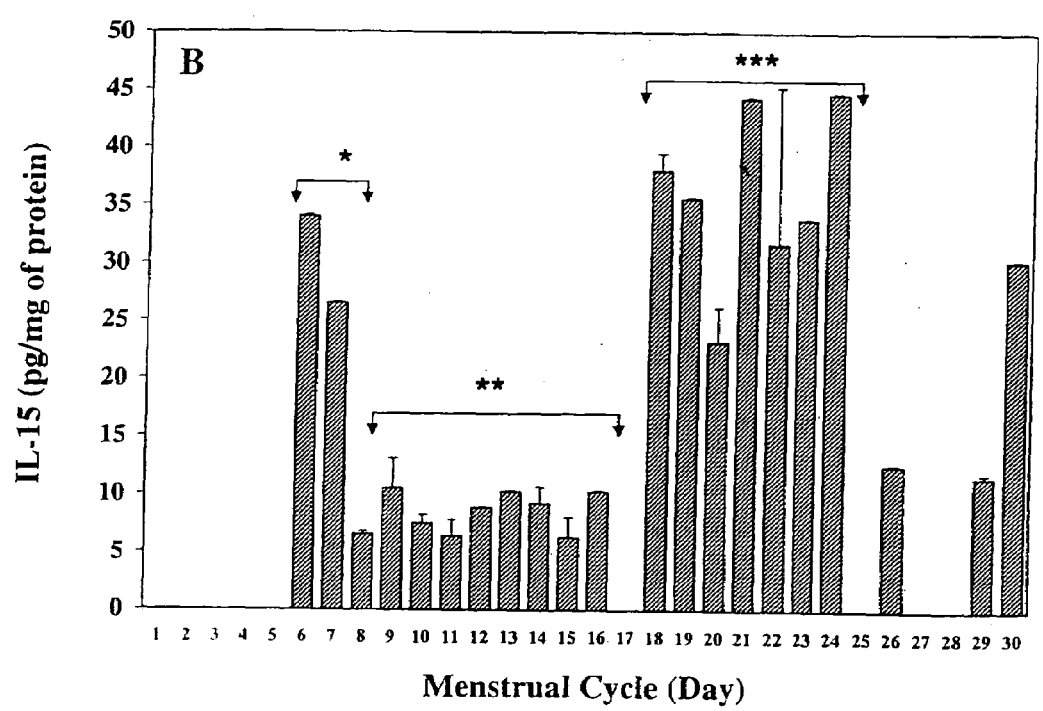

In contrast with the IL-13 results, FIG. 3B shows that IL-15 protein production was low during the proliferative and the late secretory phase, whereas peak production occurred during the early-mid secretory phase, and prior to the onset of menses (P=0.03 and 0.05). Statistical values of data in FIG. 3A were as follows: * differs from  (P=0.02) and from * (P=0.03);  differs from * (P=0.05). In FIG. 3B, * differs from  (P=0.05);  differs from *** (P=0.03).

As seen in Table 1, the ratio of IL-13:IL-15 protein content during the period of their peak production (cycle days 10–15 and 18–24, respectively) and at days 21–23 of the menstrual cycle also indicated that normal endometrium expresses a significantly higher level of IL-13 than IL-15, with a substantial reduction in IL-13 expression during the secretory phase.

Figure 4:
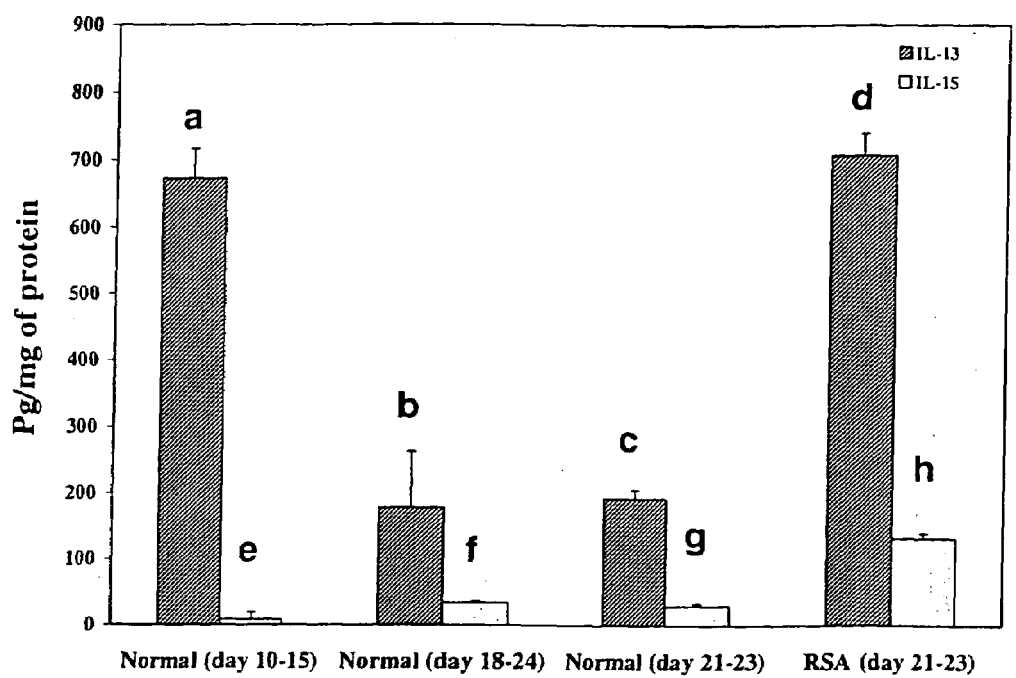
FIG. 4 is a bar graph that shows the mean±SEM level of IL-13 and IL-15 protein expression in endometrial biopsies from women with RSA at days 7–9 post LH surge (cycle days 21–23), compared with endometrial biopsies from normal fertile women at days 10–15, 18–24 and 21–23 of the menstrual cycle.

IL-13 and IL-15 protein expression in RSA. Referring now to FIG. 4, a comparison is shown of the IL-13 and IL-15 protein content in endometria of women with RSA (samples d, h), compared with samples taken from normal fertile women during late proliferative phase (cycle days 10–15; samples a, e), early-mid secretory phase (days 18–24; samples b,f), and on days 21–23 (samples c,g, corresponding to days 7–9 of the LH surge, the time of collection of the RSA biopsies). Results of this analysis showed that production of both IL-13 and IL-15 protein in the RSA samples was significantly higher (P=0.05 and 0.01) than the respective peak production values observed in endometria of normal fertile women during the three time periods analyzed during the normal cycle). Statistical values for the data shown in FIG. 4 were as follows: for IL-13, a and d differ from b (P=0.05) and from c (P=0.01). For IL-15, e differs from f and g (P=0.05); h differs from e, f and g (P=0.01).

As shown in Table 1, the ratio of IL-13:IL-15 protein expression in endometria of women with RSA was similar to normal endometrium from cycle days 18–24, but was significantly lower than cycle days 10–15. The endometrial IL-13 and IL-15 ratios in normal:RSA during cycle days 10–15, days 18–24 and days 21–23 indicated a significantly higher IL-13 and IL-15 expression in RSA compared to normal endometrium with the exception of IL-13 during cycle days 10–15 (Table 1).

TABLE 1

The Ratios of IL-13 and IL-15 mRNA and protein Expression in Endometrium of Normal and RSA

| Ratios | mRNA | Protein |
| --- | --- | --- |
| IL-13:IL-15 (Days 10–14) A | 105.6 | 82.1 (Days 10–15) |
| IL-13:IL-15 (Days-15–20) B | 17.2 | 5.2 (Days 18–24) |
| IL-13:IL-15 (Days 21–25) C | 0.51 | ND |
| IL-13:IL-15 (Days 21–23) D | 0.34 | 6.6 |
| IL-13:IL-15 (RSA) | 26 | 5.37 |
| Normal A:RSA (IL-13) | 0.01 | 0.95 |
| Normal B:RSA (IL-13) | 0.02 | 0.25 |
| Normal C:RSA (IL-13) | 0.0005 | ND |
| Normal D:RSA (IL-13) | 0.0005 | 0.27 |
| Normal A:RSA (IL-15) | 0.002 | 0.06 |
| Normal B:RSA (IL-15) | 0.03 | 0.26 |
| Normal C:RSA (IL-15) | 0.02 | ND |
| Normal D:RSA (IL-15) | 0.04 | 0.22 |

The ratios of IL-13:IL-15 mRNA and protein expression and in endometrium of normal fertile women at menstrual cycle days 10–14 (A), 15–20 (B), 21–25 (C) and 21–23 (D) and women with unexplained recurrent spontaneous abortion from days 7–9 of the LH surge (cycle days 23–23), and their ratios in normal:RSA, ND=not determined.

Immunolocalization of IL-13 and IL-15 in normal and RSA endometria. In endometrial samples from normal fertile women, immunoreactive IL-13 and IL-15 protein was primarily localized in endometrial luminal epithelial cells, with lower intensity in glandular epithelial and stromal cells and arterioles. The intensity of the immunostaining of IL-13 was higher during the mid-late proliferative phase of the menstrual cycle (days 10–14), whereas the staining of IL-15 was higher during the early-mid-secretory phase (days 21–23).

In endometria of women with RSA, the cellular distribution of immunoreactive IL-13 and IL-15 was similar to normal endometrium; however, staining intensity in all cellular compartments was increased, particularly in the glandular epithelial cells. Additionally, several cell types present among the stromal and glandular epithelial cells, possibly representing both inflammatory and immune cells, also contained immunoreactive IL-13 and IL-15 and stained with higher intensity than the endometrial cell types. Deletion of the primary antibodies, or replacement with mouse or goat IgG as controls resulted in a substantial reduction in the immunostaining intensity.

Example 2

Differential Expression of IL-13 And IL-15 In Endometria of Normal Fertile Women and Ectopic and Eutopic Endometrium of Women with Endometriosis Materials and Methods Sources of materials. All the materials for Q-RT-PCR, ELISA and immunohistochemistry were purchased from commercial sources described above. Ectopic and matched eutopic endometrial tissues and peritoneal fluids were collected with informed consent from women (N=15) who were scheduled to undergo gynecological surgical procedures. Peritoneal fluids were also collected from women (N=15) with peritoneal adhesions who were scheduled to undergo surgical procedures for benign gynecological disorders other than endometriosis. Endometrial biopsies (N=10) and peritoneal fluids (N=7) were also collected from women who were requesting permanent surgical sterilization (tubal ligation) after previously documented fertility. All the subjects were of reproductive age and were not taking any hormone therapy prior to collection of the specimens. Endometrial dating was determined by histological evaluation and the last menstrual period. The eutopic and ectopic endometrial tissues were from mid-late proliferative (N=6) and early-mid secretory (N=9) phases of the menstrual cycle and the ectopic tissues were characterized as stage II and III endometriosis. The endometrial biopsies were from late proliferative (N=5) and mid secretory (N=5) phases. The tissue specimens were divided into three portions and used for RNA and protein isolation, and fixed for immunohistochemistry, respectively.

Expression of IL-13 and IL-15 mRNA. The expression of IL-13 and IL-15 mRNA was determined using competitive quantitative RT-PCR which uses an external synthetic cRNA standard containing identical complementary sequences found in the authentic mRNA. Detailed procedures for the construction of template plasmid, generation of external cRNA standard and Q-RT-PCR are described above in Example 1.2 μg of total cellular RNA isolated from these tissues and several dilutions of the cRNA ($10^3$–$10^8$ copies/reaction) were subjected to Q-RT-PCR. The PCR products were separated on agarose gels containing ethidium bromide and the images were captured on a Kodak DC290 digital camera and stored as TIFF files. The PCR product band intensities were determined using NIH-Image software, and following normalization for their molecular weight, the ratio of the band intensities were plotted against the copy number of the cRNA/reaction. The final quantity of mRNA expression was derived from the plots where the ratio of cRNA: target mRNA is equal to 1 and reported as mean±SEM of mRNA copies/μg total RNA.

ELISA of IL-13 and IL-15. To determine IL-13 and IL-15 protein expression, the tissue specimens were homogenized in a buffer consisting of 25 mM Tris-HCl, pH 8.0, 1 mM EDTA, 150 mM NaCl, 1% Triton X-100, 5 mM NaF, and protease inhibitor cocktail (Sigma Chemical, St Louis, Mo.). The homogenates were centrifuged at 10,000×g for 15 min at 4° C., the supernatants were collected and aliquots were stored at −80° C. until assayed. Total protein content of the supernatants and peritoneal fluids was determined using the BCA assay (Pierce, Rockford, Ill.), and their IL-13 and IL-15 content was determined using ELISA kits (R & D System, Minneapolis, Minn. and Pharminogen, San Diego, Calif.) with detection limit of 32 and 3 pg/ml, respectively. The peritoneal fluid content of TNF-α receptor type I was also determined using human-specific ELISA kit with detection limit of 3 pg/ml (R & D).

Immunohistochemistry. To determine the cellular distribution of IL-13 and IL-15 protein, endometrial tissues were fixed and processed for immunohistocimisty as described above. Tissue sections were incubated with goat anti-hrIL-13 polyclonal antibody (R & D) and monoclonal antibody generated against hrIL-15 (Genzyme Co. Cambridge, Mass.) at 5 μg of IgG/ml, prepared in phosphate buffered saline, pH 7.4, containing 0.1% bovine serum albumin, as described in Zhao Y. and Chegini N., Am. J. Reprod. Immunol. 42:303–311, 1999. The sections were then exposed sequentially to biotinylated secondary antibodies and avidin conjugated horseradish peroxidase. The chromogenic reaction was carried out using 3, 3'diaminobenzidine. Deletion of IL-13 and IL-15 primary antibodies, or their replacement with goat or mouse IgG, respectively during immunostaining served as controls.

Statistics. Statistical analysis was performed as described in Example 1.

Results

Figure 5A:
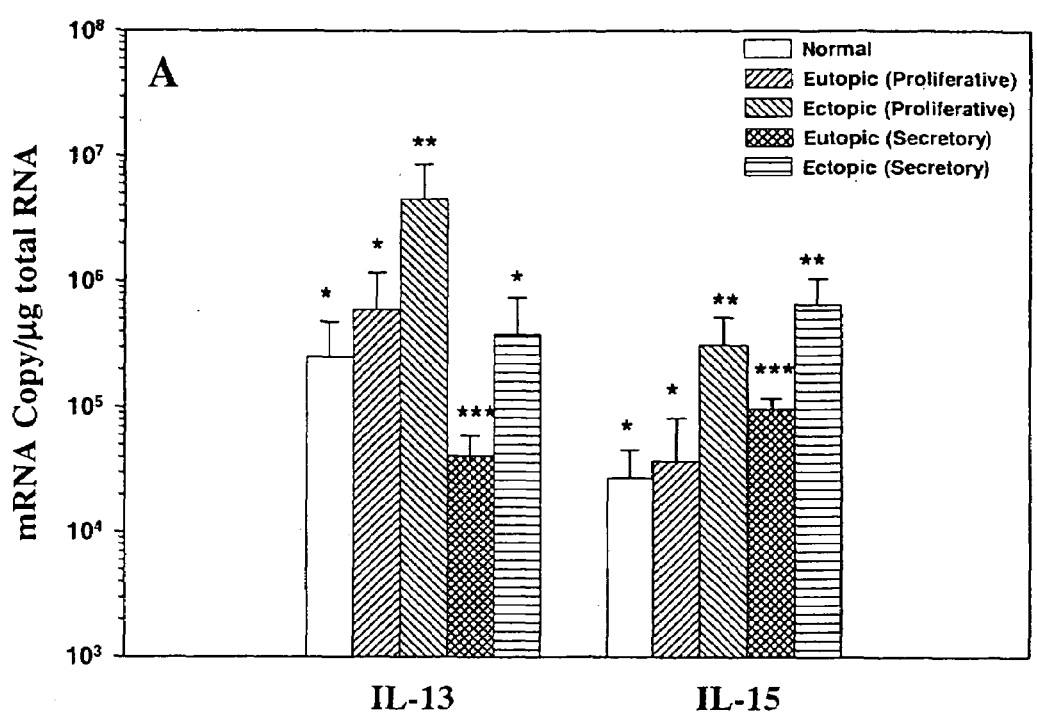
FIG. 5 is two bar graphs that show the mean±SEM of copies of IL-13 and IL-15 mRNA expression/µg total RNA (A) and IL-13 and IL-15 protein/mg of total protein (B) in ectopic and eutopic endometrium, and endometrium of normal fertile women taken during the proliferative and secretory phases of the menstrual cycle.

IL-13 and IL-15 mRNA expression in eutopic and ectopic endometrium. Referring to FIG. 5A, results are shown for Q-RT-PCR analysis of IL-13 and IL-15 mRNA expression, compared in eutopic and ectopic endometrium, taken at two stages in the cycle (proliferative and secretory phases). The results showed for both IL-13 and IL-15, ectopic endometrium expressed higher levels of mRNA than stage-matched eutopic endometrium ($P=0.05$, 0.01 and 0.03). In the ectopic tissues, IL-13 levels were higher in the proliferative phase ($P=0.03$) and IL-15 levels were higher in the secretory phase ($P=0.05$). The level of IL-13 and IL-15 mRNA expression in ectopic and eutopic endometrium was also higher than expression in endometrium of normal fertile women, with the exception of lower IL-13 expression in eutopic endometrium from secretory phase; however, these values reached statistical significance for ectopic endometrium from proliferative and secretory phase for IL-13 and IL-15 respectively (FIG. 5A, $P=0.05$). Statistical values for the data in FIG. 5A were as follows: for IL-13, * differs from  and from * ($P=0.05$);  differs from * ($P=0.01$). For IL-15, * differs from  ($P=0.03$, 0.05), and  differs from *** ($P=0.05$).

Referring to Table 2, the ratio of IL-13:IL-15 mRNA expression in ectopic and eutopic endometrium further indicated that IL-13 and IL-15 expression are elevated in ectopic endometrium, with higher expression in proliferative and secretory phase tissues, respectively. The ratio of IL-13 mRNA expression in ectopic:eutopic endometrium from the proliferative and the secretory phases was lower compared to ectopic:normal from the proliferative phase, but higher than in eutopic:normal. In contrast, the ratio of IL-15 in ectopic:eutopic endometrium was higher in both phases compared to ectopic:normal from proliferative phase, but lower than in eutopic:norrnal (Table 2).

TABLE 2

The Ratio of IL-13 and IL-15 mRNA and Protein Expression in Ectopic, Eutopic and Normal Endometrium.

| Ratios | mRNA | Protein |
|---|---|---|
| IL-13:IL-15 (Ectopic/P and S) | 12.5 and 0.58 | 10.3 |
| IL-13:IL-15 (Eutopic/P and S) | 15.9 and 0.42 | 12.7 |
| IL-13:IL-15 (Normal*) | 9.2 | 9.8 |
| Ectopic:Eutopic (IL-13/P and S) | 7.7 and 9.2 | 1.2 |
| Ectopic:Eutopic (IL-15/P and S) | 9.8 and 6.8 | 1.5 |
| Ectopic:Normal (IL-13/P and S | 18.2 and 1.5 | 1.8 |
| Ectopic:Normal (IL-15/P and S | 13.3 and 24 | 1.7 |
| Eutopic:Normal (IL-13/P and S | 2.4 and 0.2 | 1.5 |
| Eutopic:Normal (IL-15/P and S | 1.4 and 3.6 | 1.1 |

The ratios of IL-13:IL-15 mRNA and protein expression and in ectopic and eutopic endometrium from proliferative (P) and secretory (S) phase of the menstrual cycle and endometrium of normal fertile women [*represents the mean expression from proliferative and secretory phases], as well as their ratios in ectopic:eutopic, ectopic:normal and eutopic:normal. In the mRNA column, the values present the ratio in proliferative and secretory phase tissues, respectively. The values used to calculate the protein ratios are from FIG. 5B and are the mean content of proliferative and secretory phase tissues.

Figure 5B:
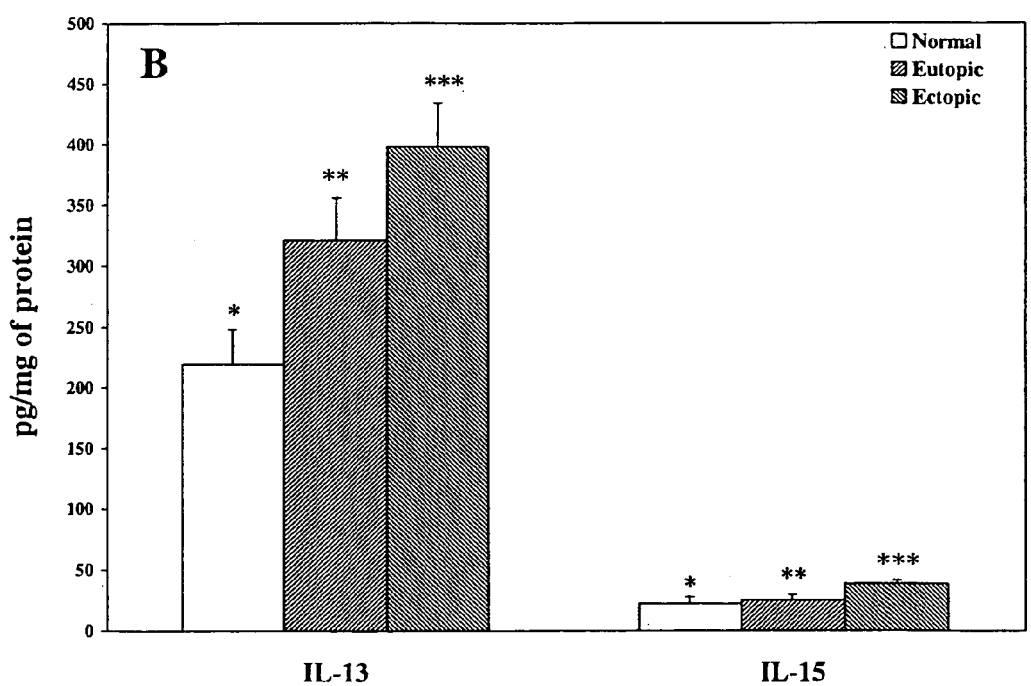

IL-13 and IL-15 protein expression in eutopic and ectopic endometrium. Referring to FIG. 5B, ectopic and eutopic endometrium also expressed IL-13 and IL-15 protein with higher content in proliferative and secretory phases, respectively. IL-13 and IL-15 protein content of ectopic endometrium was higher compared with eutopic endometrium, but it did not reach statistical significance for IL-15 (FIG. 5B; $P=0.01$, 0.05; 0.07). Compared to normal endometrium, IL-13 and IL-15 protein content of ectopic and eutopic endometrium was significantly higher ($P=0.05$). Statistical values for the data shown in FIG. 5B were the following: for IL-13, * differs from  ($P=0.05$) and from * ($P=0.01$); for IL-15, * differs from * ($P=0.05$), and  differs from *** ($P=0.07$).

As shown in Table 2, in contrast to the ratio of mRNA expression, the ratio of IL-13:IL-15 protein production in ectopic and eutopic endometrium, and their ratios in ectopic: eutopic ectopic:normal and eutopic:normal were less variable.

Immunolocalization of IL-13 and IL-15 in normal, eutopic and ectopic endometria. IL-13 and IL-15 proteins were localized by immunohistochemistry primarily in endometrial epithelial cells and were present with a lower intensity in stromal cell compartments in eutopic endometrium. They are also present in ectopic endometrium; however, with a higher intensity in particular in glandular epithelial cells compared to eutopic or normal endometrium. IL-13 and IL-15 immunoreactive proteins were also localized in several cell types representing inflammatory and immune cells that infiltrated into the endometrium and are associated with ectopic endometrial implants. In controls replacement of the primary antibodies with non-immune goat or mouse IgG or deletion of the antibodies resulted in reduction in immunostaining intensity over these cells.

Figure 6A:
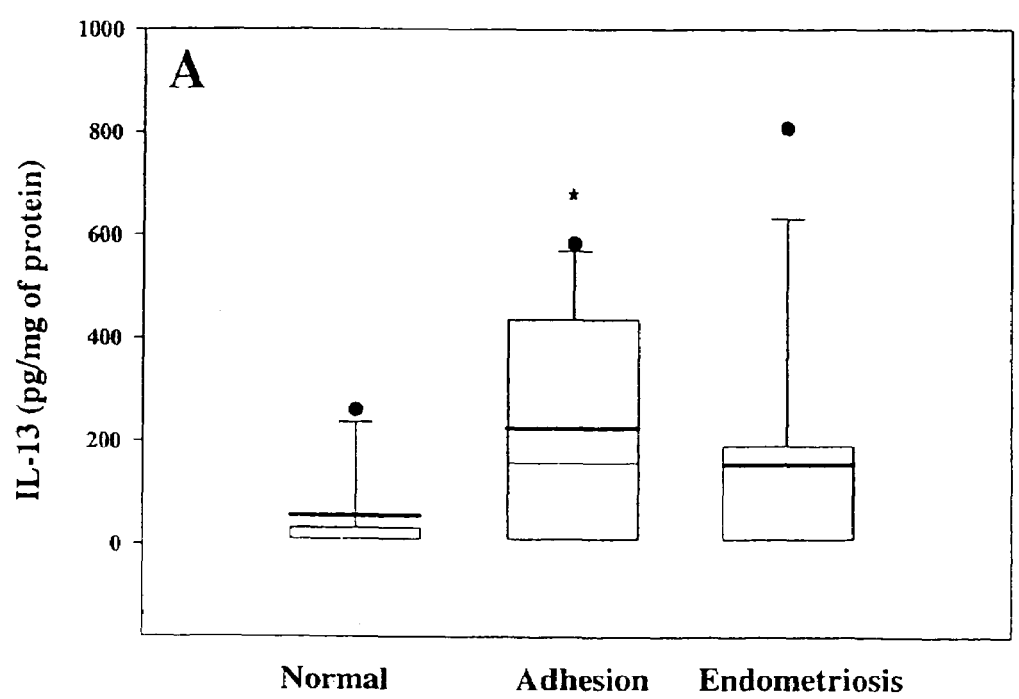
FIG. 6 is a series of notched box plots that show protein content of IL-13 (A) and IL-15 (B) as well as TNF-α receptor type I (FIG. 6C) in peritoneal fluid of normal women, women with peritoneal adhesions unrelated to endometriosis, and women with endometriosis.
Figure 6B:
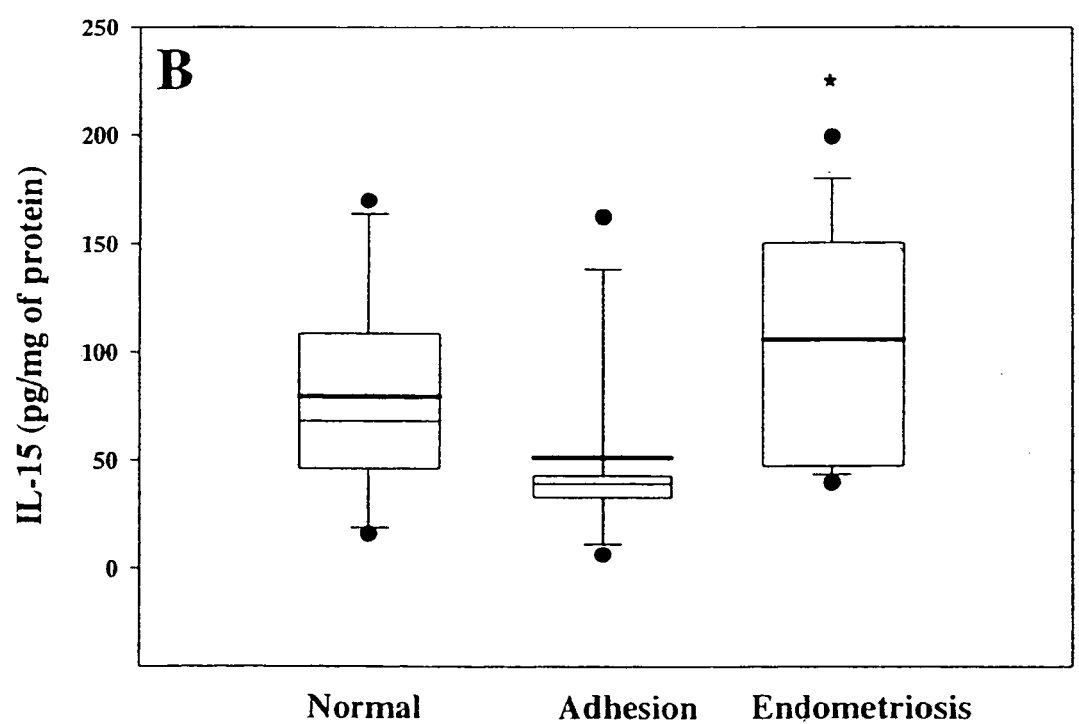
Figure 6C:
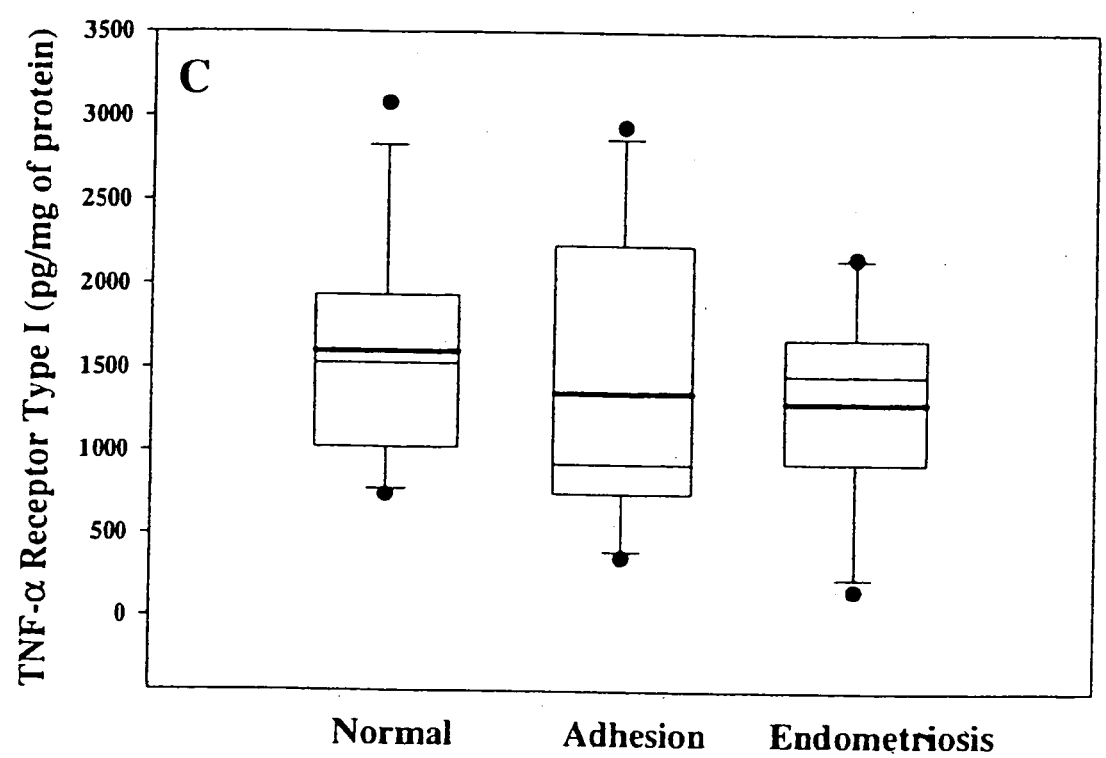

IL-13, IL-15 and TNF-α receptor type I expression in peritoneal fluids (PF). Levels of IL-13 and IL-15 protein were detected in the PF of women with and without endometriosis, and with peritoneal adhesions unrelated to endometriosis. Results are shown in FIG. 6A and B, respectively, for IL-13 and IL-15. FIGS. 6A–C are notched box diagrams, in which the vertical lines forming the box boundaries represent the distribution of the middle 50%, the thin horizontal lines within the boxes are the median, and the thick lines are the arithmetic mean values. The notches show the 95th percentile and the error bars show the 90th and 10th percentiles.

Referring to FIG. 6, substantial variability in IL-13 and IL-15 content among the PF within and between the groups was observed. The level of IL-13 and IL-15 in PF of women with endometriosis was higher, but not significantly different, compared with PF from women with normal pelvic anatomy, or with peritoneal adhesions, with the exception of IL-13 in women with adhesions compared with normal (FIG. 6A, P=0.042) and of IL-15 in endometriosis compared with adhesions (FIG. 6B, P=0.05). The IL-13 levels in PF of women with normal pelvic anatomy were low with the exception of one subject (FIG. 6A).

The ratios of IL-13:IL-15 in PF of women with and without endometriosis, and with adhesions, and their ratios in normal:adhesion, normal:endometriosis and adhesion:endometriosis are shown in Table 3. The results also revealed a higher ratio of IL-13:IL-15 in PF of women with adhesions compared to women with and without (normal) endometriosis, with ratios of 3.8, 1.6 and 0.77, respectively. Furthermore, IL-13 and IL-15 ratios in normal:adhesion, normal:endometriosis and adhesion:endometriosis normal also indicated a higher IL-13 in PF of women with adhesion and endometriosis compared to normal, and higher IL-15 in PF of women with endometriosis compared to adhesion and normal (Table 3).

TABLE 3

The Ratios of IL-13 and IL-15 Content in Peritoneal Fluids

| Ratios | Values |
| --- | --- |
| Normal:Adhesion (IL-13) | 0.26 |
| Normal:Endometriosis (IL-13) | 0.35 |
| Adhesion:Endometriosis (IL-13) | 1.35 |
| Normal:Adhesion (IL-15) | 1.3 |
| Normal:Endometriosis (IL-15) | 0.74 |
| Adhesion:Endometriosis (IL-15) | 0.57 |
| IL-13:IL-15 (Endometriosis) | 1.6 |
| IL-13:IL-15 (adhesion) | 3.8 |
| IL-13:IL-15 (Normal) | 0.77 |

The ratios of IL-13:IL-15 protein content in peritoneal fluids of women with endometriosis, women with peritoneal adhesion unrelated to endometriosis and women with normal pelvic anatomy, as well as their ratios normal:adhesion, normal:endometriosis and adhesion:endometriosis.

IL-13 and IL-15 have been shown to differentially regulate the expression of inflammatory-related cytokines such as TNF-α, indiscriminant expression of which is associated with several autoimmune and inflammatory disorders. For this reason, the content of TNF-α type I receptor in PF of women with and without endometriosis was determined. The levels of TNF-α type I receptor in PF of women with endometriosis were not significantly different compared with women with adhesions or normal pelvic anatomy (FIG. 6C, Table 4).

TABLE 4

The Ratio of TNF-α Receptor Type I in Peritoneal Fluids

| Ratios | Values |
| --- | --- |
| Normal:Adhesion | 1.18 |
| Normal:Endometriosis | 1.23 |
| Adhesion:Endometriosis | 1.04 |
| IL-13:TNF-α type IR (Normal) | 0.03 |
| IL-13:TNF-α type IR (adhesion) | 0.17 |
| IL-13:TNF-α type IR (Endometriosis) | 0.14 |
| IL-15:TNF-α type IR (Normal) | 0.05 |
| IL-15:TNF-α type IR (adhesion) | 0.04 |
| IL-15:TNF-α type IR (Endometriosis) | 0.08 |

The ratios of TNF α receptor type 1 (type IR) content in peritoneal fluids of women with endometriosis, women with peritoneal adhesion unrelated to endometriosis and women with normal pelvic anatomy, as well as IL-13:TNFα type IR and IL-15:TNFα type IR ratios.

Example 3

The Effect of Ovarian Steroids on IL-13 and IL-15 Expression in Stromal and Epithelial Cells Cells. Uterine tissue was collected and endometrial stromal cells and their culture conditions were isolated as described previously. Tang et al., Endocrinology 135:450, 1994. The isolated glandular epithelial and stromal cells were grown as monolayers in DMEM-Ham's F-12 (1:1, v/v) supplemented with 10% fetal bovine serum (FBS). Their purity and homogeneity were determined immunocytochemically by the use of monoclonal antibodies to human desmin, smooth muscle α-actin, cytokeratin 19 and vimentin.

$^3$H-Thymidine Incorporation and Cell Proliferation Assay. Endometrial epithelial and stromal cells were cultured either in 24- or 96-well dishes at approximate density of $2.5\times10^5$ and $2.5\times10^4$ cell/well, respectively, in the presence of 10% FBS for 48 h, they were then made quiescent in serum-free condition for 48 h as previously described. Tang et al., supra. The quiescent cells were incubated either in serum-free, or 2% FBS supplemented media, in the presence of appropriate concentrations of IL-13 and/or IL-15 and 2 µCi/ml $^3$H-thymidine for 48 h. The rate of incorporated $^3$H-thymidine determined as previously described. Tang et al., supra. Cell proliferation assays were preformed by seeding epithelial and stromal cells in 96-well microplates or 24 well dishes, respectively, as described above and cultured in the presence of appropriate concentrations of IL-13 and IL-15 in the presence or absence of 2% FBS. After 48 h the cells were washed and incubated with a dye solution composed of 3-(4,5-dimethylthiazol-2-yl)-2, 5-diphenyltetrazolium bromide (MTT) for 4 h at 37° C., solubilized using Promega Cell-Titer assay, and the optical density was measured using Thermomax microplate reader (Molecular Devices) at 570 nm as previously described (Tang et al., supra).

Ovarian Steroids. To determine the effect of ovarian steroids regulate IL-13 and IL-15 expression in endometrial epithelial and stromal cells, cells were subcultured in 6-well dishes at an approximate density of at $10^6$ cells/well, and incubated with phenol-free media containing 10% charcoal-stripped FBS for 48 hrs. The cells were made quiescent under a serum-free condition for 24 hrs, and then treated with $E_2$ (17 β estradiol), MPA (medroxyprogesterone acetate) or $E_2$+MPA either alone or in appropriate combinations, added to phenol-free medium containing 2% charcoal-stripped FBS (cFBS) (Hyclone, Logan, Utah). The level of IL-13 and IL-15 mRNA and protein was determined as described above after appropratie time intervals using quantitative RT-PCR and ELISA.

Results. Compared to control cells, stromal cells treated with E2 alone, MPA alone, or a combination of $E_2$ and MPA showed a statistically significant increase in IL-13 expression at various time points (e.g, 4, 6, 24, and 36 h after steroid addition). Epitheal cells treated in this manner showed a statistically significant increase in IL-13 expression to $E_2$ alone, MPA alone, or a combination of $E_2$ and MPA at 24 and 36 h, and to MPA alone a 6 h. Similarly, stromal and epitheleal cells showed a statistically significant increase in IL-15 expression at various time points in response to $E_2$ alone, MPA alone, or a combination of $E_2$ and MPA. Stromal and epitheleal cells treated with $E_2$ alone, MPA alone, or a combination of $E_2$ and MPA also exhibited modulated $^3$H-thymidine incorporation and cell proliferation compared to control cells.

Example 4

The Effect of IL-13 and IL-15 on TNFα Receptor Expression in Stromal and Epithelial Cells To determine whether IL-13 and IL-15 alter the expression of tumor necrosis factor alpha receptor, the stromal and epitheleal cells (isolated as described in Example3) were cultured, made quiescent, and then treated with IL-13 and IL-15 at appropriate concentration added to medium containing 2% cFBS. After specific time intervals the culture condition media were collected and assay for TNF-α receptor type I as previously described (Faber et al., Obstet Gynecol 98:668–673, 2001; Chegini et al., J Soc Gynecol Invest 6. 154–157, 1999) using ELISA and comparison to known concentrations of standard (R & D system).

In stromal cells treated with IL-15, a marked increase (compared to control cells) in TNFα receptor type I mRNA expression was noted at 6 h. In epithelial cells, IL-13 treated cells exhibited increased TNFα receptor type I mRNA production at 2, 4, and 6 h. A statistically significant increase in TNFα receptor type I protein expression was observed in stromal cells treated with IL-13 (at 24 and 36 h) and IL-15 (at 36 h). A statistically significant increase in TNFα receptor type I protein expression was observed in epitheleal cells treated with IL-13 at 36 h.

Other Embodiments

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

The invention claimed is:

1. A method for detecting endometriosis in a mammalian female subject, the method comprising:
   (a) providing an endometrium sample or peritoneal fluid sample derived from the subject;
   (b) analyzing the expression of a cytokine selected from the group consisting of IL-13 and IL-15 in the sample; and
   (c) correlating the expression of the cytokine with the presence or absence of endometriosis in the subject.

2. The method of claim 1, wherein said analyzing comprises quantifying the amount of IL-13 or IL-15 present in the sample.

3. The method of claim 2, wherein said analyzing comprises contacting the sample with an antibody that specifically binds IL-13 or IL-15.

4. The method of claim 1, wherein said analyzing comprises quantifying the amount of a nucleic acid that encodes IL-13 or IL-15 present in the sample.

5. The method of claim 4, wherein said analyzing comprises contacting the sample with a polynucleotide that hybridizes under low stringency conditions to the nucleic acid that encodes IL-13 or IL-15.

6. The method of claim 4, wherein said analyzing comprises performing PCR on the sample.

7. The method of claim 1, wherein said analyzing comprises analyzing expression of both IL-13 and IL-15 in the sample.

8. The method of claim 7, wherein said correlating comprises determining the ratio of IL-13:IL-15 in the sample.

9. The method of claim 1, wherein the sample is endometrium.

10. The method of claim 1, wherein the sample is peritoneal fluid.

11. The method of claim 4, wherein said analyzing comprises contacting the sample with a polynucleotide that hybridizes under high stringency conditions to the nucleic acid that encodes IL-13 orIL-15.

12. The method of claim 1, wherein the mammalian subject is human.

* * * * *